United States Patent
Ashkar et al.

[11] Patent Number: 6,165,487
[45] Date of Patent: Dec. 26, 2000

[54] METHODS AND COMPOSITIONS FOR PROGRAMMING AN ORGANIC MATRIX FOR REMODELING INTO A TARGET TISSUE

[75] Inventors: Samy Ashkar, Boston; Anthony Atala, Weston, both of Mass.

[73] Assignee: Children's Medical Center Corporation, Boston, Mass.

[21] Appl. No.: 09/058,048

[22] Filed: Apr. 9, 1998

Related U.S. Application Data

[63] Continuation-in-part of application No. 08/937,873, Sep. 29, 1997, and a continuation of application No. PCT/US97/17530, Sep. 29, 1997.
[60] Provisional application No. 60/027,123, Sep. 30, 1996.
[51] Int. Cl.[7] ........................................ A61F 2/02
[52] U.S. Cl. ................................................ 424/426
[58] Field of Search .............................. 424/426

[56] References Cited

U.S. PATENT DOCUMENTS

| | | | |
|---|---|---|---|
| 4,563,489 | 1/1986 | Urist | 524/21 |
| 4,703,108 | 10/1987 | Silver et al. | |
| 4,789,732 | 12/1988 | Urist | 530/350 |
| 4,863,732 | 9/1989 | Nathan et al. | 424/95 |
| 5,314,476 | 5/1994 | Prewett et al. | 623/16 |
| 5,328,695 | 7/1994 | Lucas et al. | 424/426 |
| 5,340,934 | 8/1994 | Termine et al. | 536/23.5 |
| 5,516,532 | 5/1996 | Atala et al. | 424/548 |
| 5,531,791 | 7/1996 | Wolfinbarger | 623/16 |
| 5,667,810 | 9/1997 | Levin | 424/520 |
| 5,670,336 | 9/1997 | Opermann et al. | 435/69.1 |

FOREIGN PATENT DOCUMENTS

| | | |
|---|---|---|
| 0251695 | 1/1988 | European Pat. Off. |
| 0321277 | 6/1989 | European Pat. Off. |
| 0419275 | 3/1991 | European Pat. Off. |
| 0495284 | 7/1992 | European Pat. Off. |
| 0585168 | 3/1994 | European Pat. Off. |
| 0637450A2 | 2/1995 | European Pat. Off. |
| 2175506 | 12/1986 | United Kingdom. |
| WO 8904646 | 6/1989 | WIPO. |
| WO 9001955 | 3/1990 | WIPO. |
| WO 9515776 | 6/1995 | WIPO. |

OTHER PUBLICATIONS

Butler, W.T. "The Nature and Significance of Oseteopontin" *Connective Tissue Research* 23:123–136 (1989).

*Primary Examiner*—Carlos A. Azpuru
*Attorney, Agent, or Firm*—Lahive & Cockfield, LLP; Elizabeth A. Hanley; Debra J. Milasincic

[57] ABSTRACT

Methods for programming a non-immunogenic matrix for remodeling into a target tissue are disclosed. Also dislosed are compositions which can promote the growth of selected tissue types in a subject. Methods for preparing the compositions are also described. The methods and compositions are useful for treatment of tissue defects in tissues such as bone, cartilage, and muscle.

35 Claims, No Drawings

METHODS AND COMPOSITIONS FOR PROGRAMMING AN ORGANIC MATRIX FOR REMODELING INTO A TARGET TISSUE

CROSS-REFERENCE TO RELATED APPLICATIONS

This application is a continuation-in-part application of U.S. Ser. No. 08/937,873 filed on Sep. 29, 1997, which is a continuation under 35 U.S.C. 119(e) to U.S. provisional application Ser. No. 60/027,123 filed on Sep. 30, 1996. This application is also a 371 continuation of PCT/US97/17530 filed Sep. 29, 1997. The present application also is related to information described in U.S. Ser. No. 08/630,734 filed on Apr. 2, 1996, which is a continuation under 35 U.S.C. 119(e) to U.S. provisional application Ser. No. 60/027,123, and is a continuation of U.S. patent application Ser. No. 08/286,273 filed Aug. 5, 1994, now U.S. Pat. No. 5,516,532, issued on May 14, 1996 and U.S. Ser. No. 08/800,745 filed on Feb. 14, 1997. The contents of each of these applications and/or issued patents are hereby incorporated by reference.

BACKGROUND OF THE INVENTION

The ability to selectively promote tissue regrowth in vivo would greatly facilitate wound healing and post-surgical recovery of patients who have suffered tissue damage or destruction due to accident or disease. Recent studies have found that certain matrix compositions can promote bone growth when implanted into damaged bone, thereby stabilizing the damaged bone and providing a means for speeding healing. However, generalized methods for promoting regrowth or repair of a variety of tissues have been elusive.

SUMMARY OF THE INVENTION

This invention provides methods and compositions for promoting regrowth or repair of a variety of tissues.

In one aspect, the invention provides a method for programming a non-immunogenic matrix for remodeling into a target biomorphic form, i.e., for preparing a target biomorphic form. The method includes the steps of providing a non-immunogenic matrix, e.g., by demineralizing a collagen source to form a demineralized organic matrix; selecting a treatment step for programming the non-immunogenic matrix for remodeling into a target biomorphic form; and treating the non-immunogenic matrix such that remodeling into the target biomorphic form occurs.

In preferred embodiments, the treatment step is selected such that the target biomorphic form is a cartilage-forming composition, a bone-forming composition, fatforming composition, or a muscle-forming composition.

In another aspect, the invention provides a method for preparing an organic material for promoting tissue growth or repair. The method includes the steps of demineralizing ground bone to provide a demineralized organic matrix; and treating the demineralized organic matrix with hyaluronic acid or a glycosaminoglycan to prepare an organic material for promoting tissue growth or repair.

In preferred embodiments, the method comprises the further step of contacting the demineralized bone matrix with a growth factor in an amount effective to promote tissue growth. In certain embodiments, the demineralized organic matrix is treated with about 1–5% by weight of hyaluronic acid or a glycosaminoglycan. In certain embodiments, the growth factor is selected from the group consisting of osteopontin, bone morphogenic protein, and bone sialoprotein. In certain embodiments, the step of demineralizing ground bone includes contacting the ground bone with at least one chelating agent. In another aspect, the invention provides an injectable, non-immunogenic composition for promoting tissue growth or repair, prepared by this method.

In another aspect, the invention provides a method for preparing an organic material for promoting tissue growth or repair. The method includes the steps of demineralizing ground bone to provide a demineralized organic matrix; and treating the demineralized organic matrix with a mineral acid under conditions such that a muscle growth-promoting factor is activated.

In another aspect, the invention provides an injectable, non-immunogenic composition for promoting tissue growth or repair. The composition comprises at least about 80% collagen matrix by weight; and a growth factor in an amount effective for promoting tissue growth. The composition is preferably substantially free of endogenous growth factors.

In certain embodiments, the composition further comprises hyaluronic acid or a pharmaceutically effective salt thereof. In certain embodiments, the growth factor is osteopontin or bone sialoprotein. In certain embodiments, the composition further comprises a glycosaminoglycan. In certain embodiments, the collagen matrix is substantially pure Type I collagen. In certain embodiments, the matrix is substantially non-migratory when injected into a living subject. In certain embodiments, the composition comprises particles between about 75 microns and about 200 microns in size. In certain embodiments, the composition comprises at least about 85% collagen by weight. In certain embodiments, the composition comprises at least about 90% collagen by weight.

In yet another aspect, the invention provides a method for promoting tissue growth in a living subject without causing inflammation in the subject. The method includes the steps of injecting into the subject an injectable, non-immunogenic composition, the composition including at least about 80% collagen matrix, and a growth factor in an amount effective for promoting tissue growth; such that tissue growth is promoted in the living subject without causing inflammation in the subject. In certain embodiments, muscle growth, bone growth, or cartilage growth is promoted.

In still another aspect, the invention provides a method for promoting the differentiation of mesenchymal cells. The method comprises contacting the mesenchymal cells with a matrix; the matrix includes an injectable, non-immunogenic composition which includes at least about 80% collagen matrix; and a growth factor in an amount effective for promoting tissue growth. The matrix contacts the mesenchymal cells under conditions such that the mesenchymal cells become differentiated.

In another aspect, the invention provides a pharmaceutical preparation, including an injectable, non-immunogenic composition for promoting tissue growth or repair, and a pharmaceutically-acceptable carrier. The injectable non-immunogenic composition includes at least about 80% collagen matrix by weight; and a growth factor in an amount effective for promoting tissue growth, and preferably is substantially free of endogenous growth factors.

In another aspect, the invention provides a method for promoting attachment and fusion of mesenchymal cells. The method includes the steps of implanting a matrix into a tissue containing mesenchymal cells, under conditions such that the mesenchymal cells attach to the matrix and become fused. The matrix includes means for attracting mesenchymal cells to the matrix; means for attaching mesenchymal cells to the matrix; and means for promoting fusion of mesenchymal cells.

In preferred embodiments, the means for attracting mesenchymal cells to the matrix comprises a chemotactic peptide. In preferred embodiments, the means for attaching mesenchymal cells to the matrix comprises a spreading domain of a growth factor. In preferred embodiments, the means for promoting fusion of mesenchymal cells comprises hyaluronic acid or a glycosaminoglycan.

DETAILED DESCRIPTION OF THE INVENTION

This invention provides compositions and methods for selectively promoting the growth of tissues in vivo.

In general, the compositions of the invention include a particulate "scaffold" which serves to stabilize the site of a tissue defect, and which can be infiltrated by cells and remodeled into a target tissue. In certain preferred embodiments, the scaffold comprises demineralized matrices derived from cartilage or bone. Alternatively, the scaffold can include a (synthetic) polymeric matrix suitable for supporting the growth of cells. The scaffold can include growth factors and other materials which promote the formation of the desired tissue type when the scaffold is implanted in the subject. Methods for preparing the compositions of the invention are described in more detail below. Additional information on collagen-based matrix preparations can be found in U.S. Pat. No. 5,516,532, issued May 14, 1996, herein incorporated by reference.

The term "biomorphic composition," as used herein, refers to a composition which, when implanted in the body of a living subject, promotes the growth of non-inflammatory tissue of a pre-determined tissue type. Examples of tissue which can be formed by injection or implantation of the biomorphic compositions of the invention include bone, muscle, cartilage, skin, fat, tendon, and the like. In preferred embodiments, the biomorphic compositions of the invention can be used to promote formation of tissues which are derived from mesenchymal cells.

The term "target biomorphic form," as used herein, refers to a composition capable of selectively promoting the growth of a target tissue, e.g., bone, muscle, cartilage, and the like.

An "endogenous" growth factor, as used herein, refers to a growth factor present in a naturally-occurring matrix without addition of additional growth factors from an external source. For example, whole natural bone can contain endogenous growth factors, which can be removed by extraction, proteolysis, and the like.

The term "subject" is intended to include vertebrates, more preferably warm-blooded animals, preferably mammals, including cats, dogs, horses, cattle, swine, and humans.

In the discussion which follows, the biomorphic compositions of the invention are described for use in promoting tissue formation in the body of a living subject. However, it will be understood that the compositions can be employed to promote tissue growth in vitro, e.g., in cell culture. Thus, the compositions of the invention can be employed to grow tissues, e.g., tissue suitable for implantation or transplantation, e.g., grafting, into a host animal.

Biomorphic Compositions

The inventions provides biomorphic compositions which promote the formation of a pre-selected tissue type when implanted in the body of a living subject. The tissue type promoted by a particular biomorphic composition will be related, at least in part, to the environment for cell growth that is provided by the biomorphic composition. Without wishing to be bound by theory, it is believed that the biomorphic compositions of the invention can promote recruitment of pluripotent (non-differentiated) cells from the tissue surrounding the implant, thereby providing cells which can grow and differentiate within the implant to form a target tissue. Accordingly, chemoattractants which can attract cells of an appropriate type can be employed in the biomorphic compositions of the invention to attract the correct cell types from the surrounding tissue into the implant, as described in more detail, infra. The matrix of the biomorphic composition can also be selected to prevent invasion of the implant by differentiated cells.

The biomorphic compositions of the invention preferably provide an environment conducive to differentiation of pluripotent cells which infiltrate the implant. In a preferred embodiment, the cells are mesenchymal cells. It will be appreciated by the skilled artisan, however, that the differentiation of cells should generally be balanced with the growth and multiplication of established cells to provide new tissue. Thus, the biomorphic compositions of the invention, when implanted into a living subject, preferably provides a structured environment which allows ordered differentiation of cells within the implant. For example, without wishing to be bound by theory, it is believed that, in certain embodiments, pluripotent cells can form an aggregate within the implant, in which cells near the center of the aggregate remain undifferentiated, while secreting growth factors which promote the differentiation of cells at the periphery of the implant, thereby producing a target tissue.

Other considerations include the size of the matrix particles (discussed further infra), and the spacing of the particles. It is believed that the interstitial space between particles of the matrix can be important in excluding certain large cells (such as keratinocytes or lymphocytes) from entering the implant. In addition, in certain embodiments in which vascularization of the implant is desired (e.g., when the target tissue type is bone or muscle), it is preferable to employ a matrix which provides sufficient interstitial space to permit the formation of vascularization in the implant (e.g., 70–100 microns between particles). Conversely, vascularization is inhibited by interstitial spaces less than about 70 microns in size; thus, for formation of tissues such as cartilage in which vascularization is not desired, smaller interstitial spaces can be employed by using smaller matrix particles and/or higher densities of matrix.

Formation of Inert Matrix

The compositions of the invention include an inert matrix which functions as a "scaffold" for the biomorphic composition. Inert matrices suitable for use in the present invention generally are substantially non-immunogenic, that is, the inert matrix does not provoke a substantial immunogenic response, such as inflammation, when injected or implanted in a living subject. Suitable inert matrices are known in the art, and include, e.g., particles of inert, non-immunogenic substances such as silicone, Teflon, and collagen, e.g., from demineralized bone powder. An inert matrix preparation is preferably sized to permit easy handling (e.g., by injection), while being resistant to migration after placement at a target site in vivo, as described in more detail infra. An inert matrix is preferably flexible enough to permit cell growth and attachment to the implant.

A particularly preferred inert matrix is derived from bone by demineralization of bone powder. Such inert matrices can be prepared according to several methods. Two methods for producing an inert matrix are described in Examples 1 and 2, below. In general, the methods involve treating bone with chelating or leaching agents to remove minerals from the bone, preferably without significantly disrupting the triple-helical nature of the collagen fibers present in the bone. It will be understood that other sources of triple-helical Type I collagen can be used in the compositions and methods of the invention.

Inert matrices prepared by the methods described herein, and useful for the preparation of the bone- and muscle-forming matrices described below, can be characterized in several ways. In preferred embodiments, the inert matrix is prepared from demineralized bone, and has a calcium concentration of less than about 100 mg/gm, more preferably less than about 50 mg/gm, less than about 20 mg/gm, less than about 10 mg/gm, or less than about 1 mg/gm of the matrix (w/w).

Chelating agents useful in demineralizing bone are known in the art. Exemplary chelating agents include chelators of Ca(II), including, for example, EDTA, EGTA, citrate, and the like. The bone, preferably ground bone, is treated with chelating reagents in an amount and for a time sufficient to remove calcium from the bone. The residual calcium present in the inert matrix is preferably present at a level not greater than about 100 mg/gm matrix, more preferably less than about 50 mg/gm, less than about 20 mg/gm, less than about 10 mg/gm, or less than about 1 mg/gm of the matrix (w/w).

If desired, the phosphate concentration of bone can be further lowered by treatment with agents such as phosphatase, and other agents known to the ordinarily skilled artisan.

It is frequently advantageous to perform repeated extractions and washings of the ground matrix to reduce the amount of calcium, phosphate, and other mineral matter to an acceptable level, and to remove any components of the matrix which could otherwise provoke an inflammatory response. As described in the Examples, below, repeated and/or prolonged washing of the matrix is effective in producing an inert, non-immunogenic matrix having a low level of minerals.

Washing or leaching solutions can comprise protease inhibitors, if desired, to prevent proteolysis of matrix components. Such protease inhibitors are not required, however, and fully active biomorphic compositions can be prepared without use of protease inhibitors. In embodiments in which protease inhibitors are present, such inhibitors will generally be selected to inhibit enzymes such as metalloproteases, serine proteases, cysteine proteases, cathepsins, and phosphatases. Exemplary enzyme inhibitors include the following: phenylmethylsulfonyl fluoride, benzamidine, epsilon-amino caproic acid, , β-hydroxy mercuribenzoate, pyrophosphate, sodium fluoride, sodium orthovanadate, levamisole, and pepstatin A (all available from Sigma Chemical Co, St. Louis, Mo.).

In preferred embodiments, the inert matrix comprises at least about 80% protein by weight, more preferably at least about 85% protein by weight, more preferably at least about 90% protein by weight, and most preferably at least about 95% protein by weight.

In certain preferred embodiments, the total protein of the matrix comprises at least about 80% collagen by weight, more preferably at least about 85% collagen by weight, more preferably at least about 90% collagen by weight and most preferably at least about 95% collagen by weight.

The presence of Type I triple-helical collagen can be detected by examining a collagen sample under a polarizing light microscope. Triple-helical collagen has a distinctive birefringence diagnostic of the undenatured state. Thus, an inert matrix (or a biomorphic matrix) prepared according to the methods described herein can be assayed for the presence of triple-helical collagen by examination of the material under polarized light. Also, triple-helical collagen is highly resistant to gelatinases.

In preferred embodiments, the collagen is substantially pure Type I collagen. The hydroxyproline/proline ratio of pure Type I collagen is about 0.6. Accordingly, the hydroxyproline/proline ratio of the protein of the inert matrix is at least about 0.4, more preferably at least about 0.50, and most preferably at least about 0.55.

The inert matrix is preferably prepared in the form of particles. In preferred embodiments, the particles are sized so as to permit injection of the inert matrix particles through a needle, e.g., a hypodermic needle, e.g., a 28-gauge needle. Thus, in preferred embodiments, the particles are not larger than about 200 microns mean diameter. The particles are preferably sized to prevent significant migration in the subject's body. Migration is a function of several factors, including the ability of cells to infiltrate or engulf the particles. The ability of cells to engulf the particles can depend upon the "effective size" of the particles, i.e., the ability of the particles to pass through cell or tissue pores (e.g. interstitial spaces). Such pores can be charged; particles of the same charge will be repelled by the pore, and will therefore have a larger effective size, that is, will be hindered in the ability to pass through cell or tissue pores (e.g. interstitial spaces). In general, particles larger than about 75 microns are not migratory when implanted. Smaller particles, e.g., particles between about 50 microns and about 75 microns, may not be migratory where the particles are charged, especially where the charge is the same as the charge on cell or tissue pores.

Matrix particles of any desired size can be prepared according to the methods described herein, or according to methods known in the art. For example, ground particles of matrix can be passed through sieves of decreasing size, until a suitable particle size is reached. The matrix material can be sized at any time during the preparation of the inert matrix. Conveniently, the particles are screened prior to treatment with chelating agents. The process of removing calcium and other minerals from bone is substantially faster when the bone is first ground into particles, as compared to whole bone.

The inert matrix preferably is substantially non-immunogenic, that is, does not produce a substantial inflammatory response when implanted, and is not rejected by the host animal. Importantly, the matrix is inert and non-immunogenic when the matrix is prepared from bone obtained from a species different from the host animal. Thus, inert matrix can be prepared from readily available sources of bone, such as bovine bone, regardless of the species of the subject. The inert matrix also does not substantially promote the formation of any tissue when the matrix alone is implanted (e.g., the matrix without any additional growth factors), although some capsule formation may be noted after implantation. The inert matrix is also preferably stable (e.g., is not resorbed) after extended time periods, as evidenced by stable size and mass of implanted inert matrix after one year in test subjects.

Formation of Biomorphic Compositions

Biomorphic compositions are preferably formed by treatment of an inert matrix, e.g., an inert matrix as described herein, with growth factors or other substances which promote the recruitment, growth, or differentiation of cells appropriate for formation of the pre-selected target tissue.

Such factors can be added to an inert matrix by methods which will be routine for one of ordinary skill in the art. For example, as described infra, the inert matrix can be stirred with a solution or suspension of a growth factor and then lyophilized to provide a dried matrix which includes the growth factor. In preferred embodiments, growth factors and other materials added to the inert matrix substrate are physically trapped within the matrix, or adsorbed into or onto the matrix, but are not covalently linked to the matrix. Thus, for example, growth factors can be immobilized within the matrix through interactions such as ionic and hydrophobic interactions, rather than covalent bonds.

Bone-Forming Compositions

In one embodiment, a matrix useful for promoting the growth of bone in a subject can be prepared from demineralized bone, e.g., the inert matrix described above. For example, bone (e.g., mammalian bone, e.g., bovine or human bone) can be treated with reagents to demineralize the bone without substantially denaturing the collagen matrix present in the bone. Selection of appropriate extracting and washing steps can provide a matrix which contains the growth factors necessary for the formation of new bone in a subject, as can be determined by use of assays as described below. Alternatively, a bone-forming matrix can be prepared from an inert demineralized matrix, as described above and in Example 4, below, by addition of appropriate growth and attachment factors to the inert demineralized matrix.

Thus, as described in more detail below, an inert matrix (e.g., prepared from bone by treatment with chelating agents, followed by washing to remove unwanted impurities, as described herein), is treated with bone growth factors, such as osteopontin, bone sialoprotein (BSP) and hyaluronic acid (see, e.g., U.S. Pat. No. 5,340,934 to Termine et al., and references cited therein). A preferred bone growth factor is osteopontin. Osteopontin (OPN) is a cell adhesion protein first identified in bone, but now associated with other tissues as well. Osteopontin is a phosphorylated glycoprotein containing an RGD cell-binding sequence. In mineralized tissues, OPN is expressed prior to mineralization and regulated by osteotropic hormones, binds to hydroxyapatite, and enhances osteoclast and osteoblast adhesion. Although the exact function of OPN is yet unknown, possibilities include a role in the recruitment of bone precursor cells to a site of mineralization, and a role in protection against bacterial infection (Butler W T, Connect. Tissue Res. 23,123–136, 1989).

The resulting matrix can promote the growth of bone in vivo. Other bone growth factors such as bone morphogenetic protein (BMP) can also be provided to promote bone growth (see, e.g., U.S. Pat. No. 5,670,336 to Oppermann et al., and references cited therein). Additional compounds such as decorin (biglycan) can be provided in the biomorphic composition to regulate the rate of mineral growth in the newly-formed bone. Addition of thrombospondin to the biomorphic composition permits the rate of vascularization to be slowed, if desired. For other references to growth factors (e.g., cytokines) which may be useful in the present invention, see, e.g., U.S. Pat. No. 5,667,810 to Levin, and references cited therein.

Without wishing to be bound by theory, it is believed that the formation of bone by the compositions of the invention proceeds by infiltration of cells into the implanted composition, attachment of the cells to the matrix of the implant, and fusion (or aggregation) of the cells to form bone. The infiltration of cells, e.g., mesenchymal cells, can be promoted by the presence in the composition of a factor known to promote bone growth, e.g., as described herein. Attachment of such cells to the matrix can also be promoted by addition of a suitable factor. It is believed that Type I collagen provides a suitable environment for attachment of cells, and Type I collagen (preferably a substantially purified, non-immunogenic Type I collagen) is accordingly a preferred matrix for a bone-forming biomorphic composition. Fusion of cells can be promoted by use of a suitable factor in the composition (e.g., hyaluronic acid (HA) or glycosaminoglycans (GAGs), as described below). HA is also believed to provide additional spacing between particles of the matrix, e.g., when the matrix particles are coated with a layer of HA. It will be appreciated that each of the steps can be promoted by addition of a factor specific for that step; alternatively, one factor can provide more than one function. For example, it is believed that osteopontin promotes both attraction of cells to the implant (infiltration) and attachment of cells to the matrix. In preferred embodiments, a bone-forming composition of the invention comprises one or more factors which promote cell infiltration, cell attachment to the matrix, and cell fusion. It is believed that bone formation requires the infiltration of macrophages into the implant; thus, an implant which permits infiltration of macrophages is preferred. Osteopontin is a specific recruiter of macrophages; therefore, a bone-forming composition preferably includes osteopontin in an amount effective to recruit macrophages into the implant from the surrounding tissue.

In one embodiment, the inert matrix is treated with osteopontin, BSP, and hyaluronic acid or a glycosaminoglycan. The matrix can be suspended in buffer, and the growth factors then added to the buffer, followed by lyophilization of the suspension to yield a dry matrix. In preferred embodiments, osteopontin is added to the matrix in the range of about 0.05% to about 0.5% (w/w when dry), more preferably about 0. 1% w/w. When BSP is added to the matrix suspension, BSP is preferably added to the matrix in the range of about 0.001% to about 0.1% (w/w when dry), more preferably about 0.01% w/w. Interestingly, when the composition is made without osteopontin, little or no bone formation occurs. Accordingly, osteopontin is a preferred bone growth factor. BSP, although preferred, is not required for bone formation. However, mineralization is faster in the presence of BSP.

Hyaluronic acid (HA) or a glycosaminoglycan (GAG, e.g., dermatan or chondroitan sulfate) can provide a modified surface conducive to tissue formation. Accordingly, the bone-forming composition preferably comprises hyaluronic acid. In preferred embodiments, hyaluronic acid is added to the matrix in the range of about 0.05% to about 0.5% (w/w when dry), more preferably about 0.1% w/w. Similarly, when glycosaminoglycans are used in addition to, or instead of, hyaluronic acid, the GAG (or GAGs) can be added to the matrix the range of about 0.05% to about 0.5% (w/w when dry), more preferably about 0.1% w/w.

It will be appreciated that the inert matrix can be introduced into the body of a subject, and the above-identified factors (i.e., osteopontin, BSP, and hyaluronic acid or a glycosaminoglycan) can be introduced (e.g., by injection) into the implanted matrix. This in situ formation of a biomorphic device is suitable for, e.g., optimizing the activity of the implant after implantation, thereby permitting the biomorphic composition to be tailored to any application.

Also, while the examples below describe the formation of biomorphic matrices which are dried to produce a material suitable for resuspension in a solvent, the inert matrix., as a suspension, can be combined, e.g., ex vivo, with any factors necessary to the function of the biomorphic composition, and the in situ constituted composition injected or implanted as described herein.

In general, the bone-forming compositions of the invention are infiltrated by macrophages within one day after implantation. Angiogenesis of the implant generally occurs in about one week, followed by mineralization of the infiltrated implant. Mineralization can occur, after about three weeks, although the time course of mineralization can vary depending upon the composition of the implant. For example, a biomorphic composition comprising osteopontin, BSP, and hyaluronic acid will, after implantation, become mineralized more rapidly than a similar composition which does not include BSP.

Cartilage-Forming Compositions

Compositions which promote the growth of cartilage tissue can be prepared by methods similar to the methods described above for bone-forming compositions, with the difference that no bone-forming factors are added to (or substantially present in) the composition. Cartilage-forming compositions are preferably formulated to promote the growth of chondrocytes. A preferred matrix for a cartilage-forming implant is Type II collagen. Addition of HA or GAGs to an inert matrix as described above, provides a composition which promotes the formation of cartilage when implanted in a subject. For example HA can be added at a concentration of about 0.5–5.0 mg/ml or GAG at a concentration of about 0.1–1 mg/ml can be added to promote cartilage formation. A preferred GAG is chondroitan sulfate.

In general, cartilage-forming compositions will be formulated to avoid or prevent angiogenesis in the implant. If substantial angiogenesis occurs, the initially-formed cartilage tissue can be converted to bone, which can be a disadvantage in certain applications. As described above, the addition of inhibitors of angiogenesis, or selection of appropriately-sized matrix particles, can slow or inhibit angiogenesis.

The cartilage formed by the inventive compositions can be fibrous cartilage, but more preferably is hyaline cartilage.

The assay methods described above can be employed to determine whether a particular composition possesses cartilage-forming activity when implanted. For example, histological examination of an implant after a period of, e.g., seven days, will reveal the presence or absence of cartilaginous tissue.

Muscle-Forming Compositions

Muscle-forming compositions preferably include Type I collagen as the inert matrix. Muscle-forming compositions can be prepared from ground demineralized bone, which can be prepared as described above and in Examples 1 and 2 for the inert matrix. However, if the procedure of Example 1 is followed, a preferred preparation omits the final high-salt (1 M NaCl) washing steps. It has now been found that omitting the high-salt wash results in higher muscle-formation activity when the matrix is treated as described below and implanted into a subject.

The inert matrix, formed as just described, is then treated with a mineral acid, e.g., HCl, e.g., at a concentration of from about 0.1 N to about 2 N, for a time from about 1 hour to about 48 hours. Acids other than HCl have been found to be considerably less effective at producing a muscle-forming composition. The skilled artisan, in view of the teachings herein, will be able to select appropriate conditions which result in muscle-forming activity of the composition, without substantially degrading the triple-helical nature of the collagen of the matrix.

After the acid-treatment step, the resulting composition is treated, e.g., repeatedly washed or neutralized with a base, e.g., ammonium carbonate, to remove traces of acid. The material can then be lyophilized and stored prior to implantation, or can be implanted directly after neutralization.

Without wishing to be bound by theory, it is believed that acid treatment of the inert matrix may release or activate an endogenous muscle-forming factor present, but not active, in the inert matrix. Although in certain embodiments, a muscle-forming composition can include a growth factor such as muscle morphogenic protein (see, e.g., U.S. Pat. No. 5,328, 695 to Lucas et al.), in a preferred embodiment, a muscle-forming composition contains no exogenous growth factors.

Preparations of Biomorphic Compositions

Biomorphic compositions can be prepared as suspensions of matrix particles suspended in a pharmaceutically acceptable vehicle. The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition.

Alternatively, biomorphic compositions can be prepared as gels, pastes, putties, semi-solids or solids, which can be shaped, formed, extruded, or otherwise processed before implantation, and which can be shaped or formed after implantation to conform to a desired shape or size, e.g., of a tissue defect.

Accordingly, biomorphic compositions can be introduced into the body of a subject by injection or by surgical implantation at a target site. The compositions can be constituted so as to occupy a defined space or cavity in the body (e.g., to fill a cavity left by the surgical removal of tissue), or can be sufficiently fluid to occupy any space, whether regular or irregular, into which the composition is placed.

Uses for Biomorphic Compositions

The biomorphic compositions of the invention can be implanted or injected into the body of a subject to promote the growth of a variety of tissues. Thus, biomorphic compositions are useful in a variety of procedures for repairing, replacing, or augmenting tissues of the body.

For example, a bone-forming biomorphic composition can be used to promote healing of surgically-altered bone (e.g., after removal of osseous tumors or extraction of teeth); or to promote healing, e.g., in peridontitis or of fractures (e.g., non-union fractures) or to form new bony structures.

Bone-forming implants are thus useful in many applications for which autologous bone transplants are currently performed.

Similarly, muscle-forming biomorphic compositions can be used to replace muscle, e.g., muscle tissue removed by surgery or damaged through accident. Biomorphic compositions which form cartilage can be used for replacement or repair of cartilage, e.g., cartilage removed in surgical procedures (e.g., arthroscopic removal of torn cartilage) or cartilage damaged, e.g., by tearing. Biomorphic compositions which form skin have applications to healing of wounds and to skin grafts, e.g., to assist burn healing.

Biomorphic compositions can also be useful in plastic surgery applications, e.g., for lip augmentation, or for surgical reconstruction, e.g., of cartilaginous structures such as ears or nose.

Assays for Biomorphic Activity of Compositions

It is important to be able to determine whether a given composition has activity as a biomorphic composition, e.g., for quality control in the preparation of biomorphic materials. The activity of a given composition can readily be determined by assays which will be routine to the skilled artisan.

Thus, for example, a biomorphic composition can be implanted in a test animal, and the effect of the implanted composition assayed at one or more time points to determine the in vivo efficacy of the composition. Assays can be performed in vivo or ex vivo, as described herein, or according to known methods of diagnosis, histology or pathology.

For example, a bone-forming biomorphic composition can be assayed by subcutaneous implantation in a test animal such as a mouse. After a selected time period, e.g., 24 hours or one week, the implant can be removed and assayed to determine the infiltration of cells into the implant. For example, the implant can be digested with a neutral protease or a collagenase to degrade the collagenous matrix and release any cells that have infiltrated the implant. The released cells can then be sorted and counted, e.g., using FACS, to determine the type and number of cells present in the implant.

Alternatively, the implant can be dissected out of the test animal and then sectioned and stained for microscopic evaluation, as is routine in pathology laboratories.

A bone-forming composition will in general be infiltrated by macrophages within one day after implantation in a mouse. Thus, a suitable screening assay for activity of a bone-forming composition is to implant the composition into a mouse and examine the implant for macrophage infiltration after 24 hours. Also, blood vessels are generally present in the implant after about three weeks; this process is readily determined under a microscope.

The activity of a biomorphic composition in a test animal can also be assayed by examining the animal without removing the implant. For example, simple palpation of a subcutaneous implant can be sufficient to determine, e.g., whether mineralization of a bone-forming implant has occurred. Also, techniques such as magnetic resonance imaging, bone scanning, or CAT scanning can be employed to examine the effect of the biomorphic composition in vivo. Bone formation can be readily monitored by X-ray imaging once mineralization of the implant has begun.

The invention will next be described in connection with certain non-limited examples:

EXAMPLE 1

Preparation of an Inert Matrix: Procedure A

The cartilage and/or bone is cleaned, ground in a liquid nitrogen cooled mill, passed through a sieve having a nominal size of 200 microns, and collected with a sieve having a nominal size of 100 microns. The particles were then washed four times with ice cold (0 to 4° C.) HEPES buffer, pH 8.2, containing 0.5M KCl (Buffer A). 100 gm (wet weight) of bone was demineralized with three changes of 4000 ml prechilled (0 to 4° C.) 20 mM HEPES buffer, pH 8.2, containing 0.5M EGTA (Buffer B), at a temperature of 2° C., until the calcium concentration was below about 100 mg/gm bone. The bone particles were then collected by filtration or by centrifugation, for example in a GSA rotor at 4000×g for 30 minutes. The pellet was then washed three times with HEPES buffer, pH 8.2, containing 1 M NaCl (Buffer C), then resuspended in Buffer C and stirred overnight at 4° C. The matrix was collected by filtration and extracted stirred twice more with Buffer C. The matrix was collected and washed, then suspended in 20 mM HEPES buffer, pH 8.2, containing 1 M ammonium bicarbonate (Buffer D) and stirred overnight at 4° C. The matrix was collected and washed three times with 0.1 M sodium bicarbonate solution, pH 7.4. Finally, the wet matrix was dried under vacuum and stored at −20° C. until use.

The resulting material was substantially non-immunogenic and had the following properties on analysis:

| | |
|---|---|
| Total protein: | 84% by weight |
| Total collagen: | 80% by weight |
| Collagen as a percentage of total protein | 95.2% |
| Minerals: | 12% by weight |

EXAMPLE 2

Preparation of an Inert Matrix: Procedure B

The inert matrix was made by the following procedure: 100 gm ground bone, prepared as in example 1, was demineralized with 500 ml of chilled buffer containing 0.2 M EDTA, pH 8.2, at 2° C., for nine days. The buffer was changed every third day. After nine days, the residual matrix was collected and extracted with 500 ml of 0.2 M sodium citrate, pH 5.2, until the calcium concentration was below about 20 mg/gm matrix. The particles were then collected by filtration and washed three times with one liter of ice-cold water. The wet matrix was dried under vacuum and stored at −20° C.

The resulting material was substantially non-immunogenic and had the following properties on analysis:

| | |
|---|---|
| Total protein: | 94% by weight |
| Total collagen: | 96% by weight |
| Collagen as a percentage of total protein | 100% |
| Minerals: | 4% by weight |

EXAMPLE 3

Preparation of Muscle-Forming Matrix

A demineralized matrix was prepared by the method described in Example 1, supra, up to the final high-salt (1 M NaCl) washing step. At this point, the matrix was extracted with 1 N HCl at 4° C. overnight. The matrix was then collected and residual acid was neutralized with ammonium bicarbonate. Lyophilization yielded a dry matrix, which was stored at −20° C. prior to use.

EXAMPLE 4

Preparation of Bone-Forming Matrix

The inert matrix prepared in Example 1, supra, was suspended in physiological saline (PBS) with 0.1% (w/w) osteopontin, 0.01% (w/w) bone sialoprotein and 0.1% (w/w) of high-molecular-weight hyaluronic acid. The suspension was dried down to yield a dry matrix, which stored at −20° C. prior to use.

The inert matrix prepared in Example 2 was treated in the same way, and a similar material resulted.

EXAMPLE 5

Formation of Bone in vivo with Bone-Forming Matrix

The bone-forming matrix of Example 4 (50 mg, suspended in saline (PBS) at a concentration of 200 mg/ml) was injected subcutaneously over a shoulder blade of 4 week old c57 blk mice. The implants were removed one week, four weeks, or six months after implantation. The removed implants were fixed with 1% formaldehyde in PBS, embedded in paraffin, and thinly sectioned. The sections were stained with Hematoxilin and eosin and examined under a microscope at 40×, 200×, or 400× magnification. Control mice were injected with the inert matrix material of Example 2.

The implanted inert matrix showed a thin capsule around the implant, and very little cell infiltration into the implant, even after six months. The size and mass of the inert implant did not significantly change over the course of the experiment.

In contrast, the bone-forming matrix implants showed rapid infiltration of mesenchymal cells and macrophages after only one week. Implants of the bone-forming matrix also showed rapid angiogenesis in the implant (visible after one week). Some inflammatory nodules were seen, but the implant did not provoke a generalized inflammatory response.

For analysis of implants four weeks after injection, the implants of bone-forming matrix were removed, implanted in JB4 before sectioning, and stained with Van Kossa stain (or Safranine O with a fast green counter stain). Some implants were demineralized with 1% formic acid for three days before being embedded in paraffin. Van Kossa staining of the implants at four weeks showed abundant mineral deposition throughout the implant. Demineralized samples stained with Safranine O/fast green showed embedding of osteocytes at the periphery of newly-formed bone, and the presence of osteoblasts within the newly-formed bone. Highly organized collagen fibers could be seen, forming a periosteal collar around the immature, less-developed new bone.

EXAMPLE 6

Formation of Muscle in vivo with Muscle-Forming Matrix

The muscle-forming matrix of Example 3 (50 mg, suspended in saline (PBS) at a concentration of 200 mg/ml) was injected subcutaneously over a shoulder blade of 4 week old c57 blk mice. The implants were removed one week, two weeks, or four weeks after implantation. The removed implants were fixed with 1% formaldehyde in PBS, embedded in paraffin, and thinly sectioned. The sections were stained with Hematoxilin and eosin and examined under a microscope at 40× or 400× magnification.

After one week, muscle cells were seen within the implant; the bulk of the implant contained large numbers of undifferentiated mesenchymal cells. After two weeks, the majority of the implant was replaced by muscle tissue; Z bands were visible in many cells. After four weeks, muscle tissue had completely replaced the matrix material of the implant.

EXAMPLE 7

Repair of Bone Defects with Bone-Forming Matrix

The ability of a bone-forming composition of the invention to repair bone defects was assessed using an animal model.

Bone defects were created in the jaws of male Sprague-Dawley rats. In each animal, two 1.0 cm extraoral submandibular incisions were performed bilaterally and mucoperoteal flaps including the muscles were elevated. Two circular defects, 6.0 mm in diameter were created using a round burr and a 6.0 mm rephine at low speed under vigorous irrigation with sterile saline. The defects extended the entire width of the ramus.

The defects were randomly treated with one of four treatments. In the first (control) group, the surgical incision was closed without further treatment of the bone defect. In the second group, the bone defect was filled with an inert, non-immunogenic bone composition, prepared as described in Example 2, supra. In the third group, the bone defect was filled with rat autograft/allograft bone (obtained from genetically-identical twin litter mates). In the fourth group, the bone defect was filled with the bone-forming matrix prepared in Example 4, supra. For all animals, after treatment (if any), the muscular flap was repositioned and sutured with chromic gut sutures and the overlying skin was sutured with vicryl. Animals were sacrificed and the mandibles removed and split for separate analysis of each defect.

Results for animals sacrificed at two weeks after treatment are as follows:

The untreated control mandibles were found to have massive hematoma, and no evidence of bone or cartilage formation as seen on histology slides. Scar tissue and/or connective tissue healing appeared to have begun, and fibroblast invasion had also begun.

Bone defects treated with the inert, non-immunogenic bone composition had little bone formation. The implant was found to be cellular, with bone formation beginning on the periphery of the implant. There was no evidence of scar or fibrous healing, and little invasion of fibroblastic or muscle cells was noted.

Bone defects treated with allograft bone showed that immature bone formation had occurred; the implant was highly cellular. New bone formation was present at the periphery of the implanted graft material. No cartilage formation or fibroblastic invasion was seen.

Bone defects treated with the bone-forming matrix of the invention showed extensive trabecular formation through bone appositional growth. New bone-forming cells (osteoblasts) were attached to the implanted matrix and deposited new bone around the matrix. There was also indication of new bone formation from the periphery into the interior of the implant. The implant was less cellular than the control-treated defects. No evidence of cartilage formation was seen. Several areas of trabecular bone showed the presence of blood vessels and distinct marrow spaces.

Further results were obtained by sacrifice of the animals at four weeks post-treatment. At the four-week time point, defects filled with the bone-forming matrix of the invention were substantially indistinguishable from the surrounding bone. Bone defects treated with allograft bone showed considerable mature bone formation, although the border of the defect was still evident. Bone defects treated with the inert, non-immunogenic bone composition had some bone formation, but less than was seen with the bone-forming matrix of the invention. Unfilled defects showed little or no bone formation but were filled with connective tissue.

The results of this experiment show that the bone-forming compositions of the invention can provide new bone formation in bone defects. It is believed that the bone-forming compositions of the invention provided results equal to, or superior to, the results seen with bone allograft treatment.

EXAMPLE 8

General Overview of Factors Considered in Programming an Organic Matrix for Remodeling into a Target Tissue and Preparation of Fat-Forming Matrix To induce tissue remodeling, tissue expansion or tissue morphogenesis various factors are considered, including but not limited to the following:

Architecture of Scaffold

A scaffold or carrier used for tissue regeneration may have the following criteria:

a) The scaffold is porous. Porosity in this context is defined by the three dimensional space created by the packing of the material which allows cells to invade the resulting space with having to degrade the carrier. The porosity of the material can act as an active selective barrier to tissue invasion. Material packing that leaves a space of less than 20 microns may not allow vascularization of the scaffold but may allow fibrobasts to invade.

b) The scaffold is capable of remodeling. Remodeling in this case is defined by the ability of the invading tissue to replace the scaffold with native extracellular matrix, without an intermediate granulation tissue, scare tissue or fibrous tissue.

c) The scaffold supports direct tissue attachment without an intervening step where the incoming cells secrete an attachment molecule to allow cell attachment and transition out of S phase.

d) In certain cases, the scaffold permits the angiogenesis prior to scaffold remodeling.

Tissue Interface

For successful regeneration of tissue, direct interface with the surrounding tissue is advantageous without an intervening fibrous capsule, e.g., no foreign body reaction Tissue Specificity 1) The device actively and specifically recruits the desired cells. Type I collagen is capable of recruiting all mesenchymal cells regardless of their lineage or capability for differentiation and is capable of supporting the proliferation of recruited cells. However, type I collagen can be made specific for certain types of cells by modifying its surface to attract specific cells. For example, specific cell recruitment could be induced if collagen is modified with fibronectin or thrombospondin.

2) Once cells are recruited, the device supports the morphogenesis of the recruited cells into the specific type of tissue 3) In addition, the device selectively excludes the invasion of undesired cell types. This can be achieved in two ways a) by physically excluding certain cells from invading the device by regulating the porosity of the device, as mentioned above, and b) by redesigning the surface of the device such that undesired cells will not attach and will undergo apoptosis, programmed cell death. For example, inclusion of osteopontin in the device makes the device specific for mesenchymal cells that express CD44(v5, v6), alpha, betax integrin and heparin on their cell surface. Proper attachment of cells to osteopontin shuts down apoptosis and activate cell proliferation.

Several methods of using this approach to induce specific tissues are described above, one more example is added below.

To generate adipose tissue, a specific device is constructed by combining collagen matrix(100 mg), as described above, with fibronectin (1 ug), and osteopontin (100 ug) (secreted from immature bone cells) in 1 ml of phosphate buffered saline (PBS). This device is injected intradermally, in the fat pad or in the mammary gland of mice, and remodels within a week to adipose.

Equivalents

The contents of all references cited throughout this application are hereby incorporated by reference.

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method for programming a non-immunogenic matrix for preparing a target biomorphic form, comprising:

providing a non-immunogenic matrix;

selecting a treatment step for programming the non-immunogenic matrix into a target biomorphic form; and treating the non-immunogenic matrix such that the target biomorphic form is prepared.

2. The method of claim 1, wherein the treatment step is selected such that the target biomorphic form is a cartilage-forming composition.

3. The method of claim 1, wherein the treatment step is selected such that the target biomorphic form is a bone-forming composition.

4. The method of claim 1, wherein the treatment step is selected such that the target biomorphic form is a muscle-forming composition.

5. The method of claim 1, wherein the treatment is selected such that the target biomorphic form is a fat-forming composition.

6. The method of claim 5, wherein the step of providing the non-immunogenic matrix comprises demineralizing a collagen source to form a non-immunogenic demineralized organic matrix.

7. The method of claim 1, wherein the step of treating the non-immunogenic matrix comprises adding a growth factor to the non-immunogenic matrix.

8. A method for preparing an organic material for promoting tissue growth or repair, comprising the steps of:
   demineralizing ground bone to provide a demineralized organic matrix; and
   treating the demineralized organic matrix with hyaluronic acid or a glycosaminoglycan to prepare an organic material for promoting tissue growth or repair.

9. A method for preparing an organic material for promoting tissue growth or repair, comprising the steps of:
   demineralizing ground bone to provide a demineralized organic matrix;
   treating the demineralized organic matrix with a mineral acid under conditions such that a muscle growth-promoting factor is activated.

10. The method of claim 8, wherein the method comprises the further step of contacting the demineralized bone matrix with a growth factor in an amount effective to promote tissue growth.

11. The method of claim 8, wherein the demineralized organic matrix is treated with about 1–5% by weight of hyaluronic acid or a glycosaminoglycan.

12. The method of claim 10, wherein the growth factor is selected from the group consisting of osteopontin, bone morphogenic protein, and bone sialoprotein.

13. The method of claim 8, wherein the step of demineralizing ground bone includes contacting the ground bone with at least one chelating agent.

14. An injectable, non-immunogenic composition for promoting tissue growth or repair, comprising:
   at least about 80% collagen matrix by weight; and
   a growth factor in an amount effective for promoting tissue growth;
   wherein said composition is substantially free of endogenous growth factors.

15. The composition of claim 13, further comprising hyaluronic acid or a pharmaceutically effective salt thereof.

16. The composition of claim 14, wherein the growth factor is osteopontin.

17. The composition of claim 14, wherein the growth factor is bone sialoprotein.

18. The composition of claim 14, further comprising a glycosaminoglycan.

19. The composition of claim 14, wherein the collagen matrix is substantially pure Type I collagen.

20. The composition of claim 14, wherein the matrix is substantially non-migratory when injected into a living subject.

21. The composition of claim 14, wherein said composition comprises particles between about 75 microns and about 200 microns in size.

22. The composition of claim 14, wherein the composition comprises at least about 85% collagen by weight.

23. The composition of claim 22, wherein the composition comprises at least about 90% collagen by weight.

24. A method for promoting tissue growth in a living subject without causing inflammation in the subject, the method comprising:
   injecting into the subject an injectable, non-immunogenic composition comprising at least about 80% collagen matrix; and
   a growth factor in an amount effective for promoting tissue growth;
   such that tissue growth is promoted in the living subject without causing inflammation in the subject.

25. The method of claim 24, wherein muscle growth is promoted.

26. The method of claim 24, wherein bone growth is promoted.

27. The method of claim 24, wherein cartilage growth is promoted.

28. A method for promoting the differentiation of mesenchymal cells, comprising:
   contacting the mesenchymal cells with a matrix comprising an injectable, non-immunogenic composition comprising
   at least about 80% collagen matrix; and
   a growth factor in an amount effective for promoting tissue growth;
   under conditions such that the mesenchymal cells become differentiated.

29. An injectable, non-immunogenic composition for promoting tissue growth or repair, prepared by the method of claim 8.

30. A pharmaceutical preparation comprising an injectable, non-immunogenic composition for promoting tissue growth or repair, and a pharmaceutically-acceptable carrier, wherein the injectable non-immunogenic composition comprises
   at least about 80% collagen matrix by weight; and
   a growth factor in an amount effective for promoting tissue growth;
   and wherein said composition is substantially free of endogenous growth factors.

31. A method for promoting attachment and fusion of mesenchymal cells, the method comprising:
   implanting a matrix into a tissue containing mesenchymal cells, under conditions such that the mesenchymal cells attach to the matrix and become fused;
   wherein the matrix comprises:
     means for attracting mesenchymal cells to the matrix;
     means for attaching mesenchymal cells to the matrix; and
     means for promoting fusion of mesenchymal cells.

32. The method of claim 31, wherein the means for attracting mesenchymal cells to the matrix comprises a chemotactic peptide.

33. The method of claim 31, wherein the means for attaching mesenchymal cells to the matrix comprises a spreading domain of a growth factor.

34. The method of claim 31, wherein the means for promoting fusion of mesenchymal cells comprises hyaluronic acid or a glycosaminoglycan.

35. The method of claim 10, wherein the growth factor is osteopontin.

* * * * *